United States Patent [19]

Halpern et al.

[11] Patent Number: 4,909,262

[45] Date of Patent: Mar. 20, 1990

[54] APPARATUS FOR OBTAINING A BODY LIMB TORQUE SIGNAL

[75] Inventors: Alan A. Halpern, Kalamazoo, Mich.; Steven Lamb, Hayward, Calif.

[73] Assignee: Orthopedic Systems, Inc., Hayward, Calif.

[21] Appl. No.: 304,167

[22] Filed: Jan. 31, 1989

[51] Int. Cl.$^4$ ................................. A61B 5/10
[52] U.S. Cl. ................................. 128/774; 128/782; 33/512
[58] Field of Search ............... 128/774, 782; 73/379–381; 33/511–512, 515

[56] References Cited

U.S. PATENT DOCUMENTS

| | | | |
|---|---|---|---|
| 4,306,571 | 12/1981 | McLeod, Jr. | 128/782 |
| 4,436,099 | 3/1984 | Raftopoulds | 128/782 |
| 4,571,834 | 2/1986 | Fraser et al. | 128/782 X |
| 4,649,934 | 3/1987 | Fraser et al. | 128/782 |
| 4,804,000 | 2/1989 | Lamb et al. | 128/774 |

OTHER PUBLICATIONS

Brochure, "KIN–COM, The One & Only Complete System!"; Chattecx Corporation, undated.
Brochure, "The Weighting is Over", Isopower LE400, The Toro Company, 1986.
Brochure, "The Dynamic Cruciate Tester", Richards Medical Company, undated.
Brochure, "The New CYBEX 340 System", Cybex Division of Lumex Inc., 1987.

Primary Examiner—Angela D. Sykes
Attorney, Agent, or Firm—Bielen, Peterson & Lampe

[57] ABSTRACT

An apparatus utilizing a clamp mechanism for holding a rotating body limp. A mechanical arm is linked to the clamp mechanism and rotatably connects to a pivot member. The angular rotation of the mechanical arm about the pivot member is measured simultaneously with force exerted by the rotating body limb on the clamp mechanism. A strain gage is linked to the clamp mechanism to provide such force measurement.

12 Claims, 2 Drawing Sheets

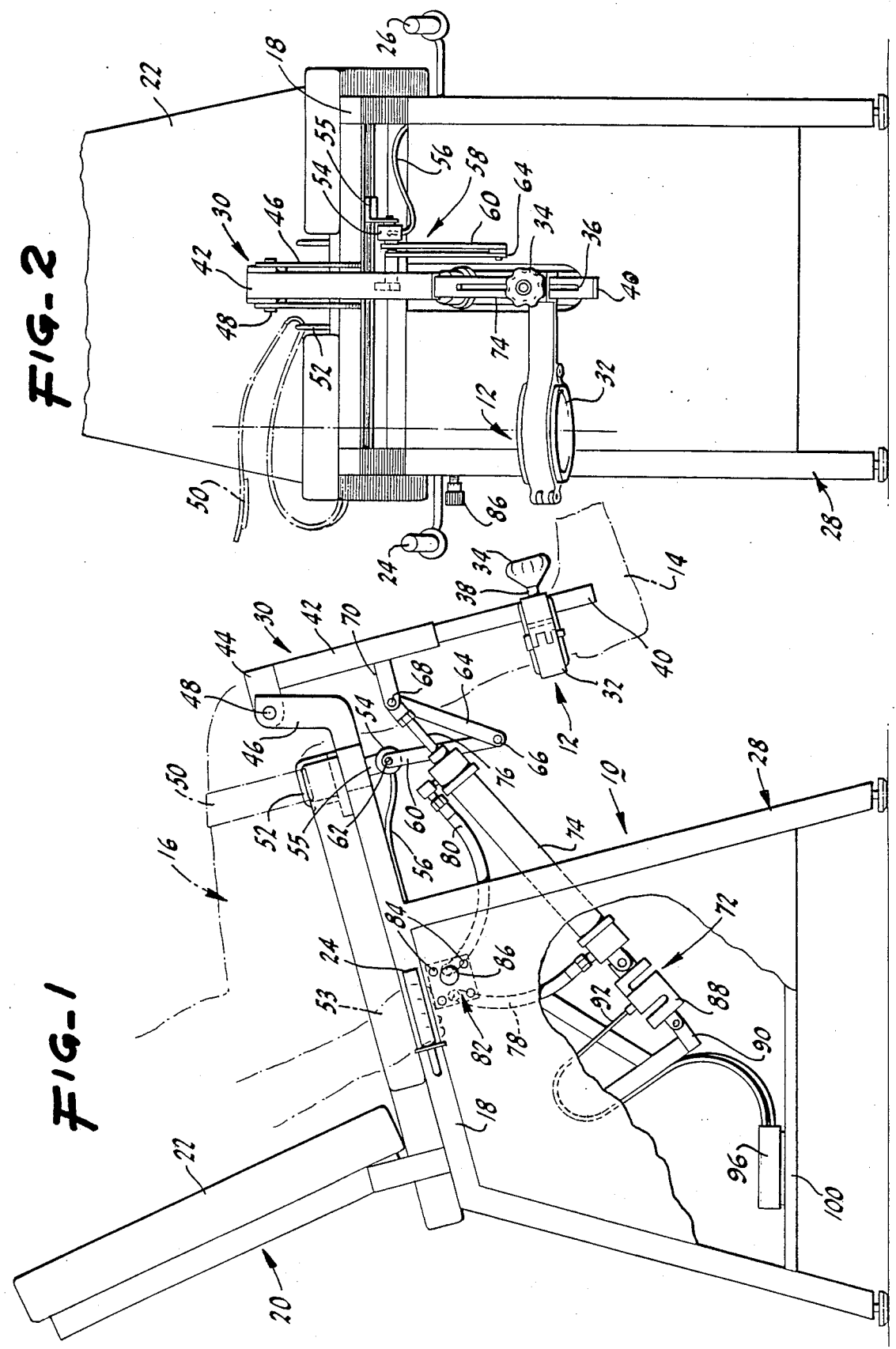

APPARATUS FOR OBTAINING A BODY LIMB TORQUE SIGNAL

BACKGROUND OF THE INVENTION

The present invention relates to a novel apparatus for obtaining a measurement signal representing the torque produced by a rotating biological limb.

Health care professionals must often measure a function of an injured limb, i.e.: the quadracep and hamstring function of a leg. Such information is often necessary before or after arthroscopic surgery or for the implementation of a rehabilitation program for a damaged limb.

In the past many devices have been marketed to test muscle performance, knee laxity and other joint patterns. For example, machines of this type include the Kin-Com manufactured by Chattecx Corporation, of Chattanooga Tenn.; the Isopower LE 400, manufactured by The Toro Company of Minneapolis, Minn.; the DCT, manufactured by Richards Medical Co., of Australia; and the Cybex 340 System, manufactured by The Cybex Division of Lumex Inc., Ronkonkoma N.Y. In all these prior devices, dynamometers and like components are included as a integral part of the same. Although accurate, dynamometers are generally very expensive and complex in their operation.

A testing apparatus which is relatively simple and inexpensive to manufacture would be a great advance in the orthopedic medical field.

SUMMARY OF THE INVENTION

In accordance with the present invention a novel and useful apparatus for obtaining a torque signal produced by a rotating limb, is provided.

The apparatus of the present invention utilizes clamp means for holding the rotating biological limb, such as a leg. Clamp means may include "quick adjust" ankle and leg straps and be rotatably attached to a platform, in the form of a chair. The clamp means is rotatably connected to a mechanical arm. An connector segment or appendage may be employed to link the mechanical arm to the clamp means such that the appendage is pivotally attached to the mechanical arm and to the clamp means. A pivot member mounts the mechanical arm to the platform, thus the mechanical arm is rotatably connected to the platform via the pivot member.

Means is also provided in the present invention for measuring the angular rotation of the mechanical arm about the pivot member. Such means may take the form of an electrical potentiometer which rotates with portion of the pivot member. The potentiometer would produce an analog signal indicating the angular rotation of the biological limb, in actuality, the rotating mechanical arm connected to the platform pivot member.

In addition means is also defined for measuring the force exerted by the rotating the biological limb on the clamp means simultaneously with the heretofore described measurement of the angular rotation of the biological limb. Such means may include a strain gage which attaches to a hydraulic cylinder, having piston shaft linked to the clamp means. The hydraulic cylinder provides mechanical resistance to the rotation of the mechanical arm. Adjusting means may also be found in the present invention for the purpose of determining the level of mechanical resistance provided by the hydraulic cylinder. Such regulating means may take the form of a valve for controlling the flow of hydraulic fluid through the hydraulic cylinder. The valve may be mounted on the platform for the sake of convenience.

The analog signal from the strain gage may be coordinated with the analog signal from the potentiometer to provide a determination of torque produced by the rotating limb.

It may be apparent that a novel and useful apparatus for obtaining a signal representing a measurement of the torque produced by a rotating limb is provided.

It is therefor an object of the present invention to provide an apparatus for obtaining a signal representing a biological limb torque which is simple and inexpensive to manufacture.

Another object of the present invention is to provide an apparatus for obtaining a signal representing the torque of a biological limb which is usable with a digital electronic microprocessor to provide graphic display information, graphical printouts, data memory, and visual feed back data for patient viewing.

Another object of the present invention is to provide an apparatus for obtaining a signal representing a biological limb torque which may be used for rehabilitation of the same after injury.

A further object of the present invention is to provide an apparatus for obtaining a signal representing torque of a biological limb which is simple to maintain and repair.

Yet another object of the present invention is to provide an apparatus for obtaining a signal representing the torque of a biological limb which is easily operated by persons having minimal training.

The invention possesses other objects and advantages especially as concerns particular characteristics and features thereof which will become apparent as the specification continues.

BRIEF DESCRIPTION OF THE DRAWINGS

FIG. 1 is side elevational view of the apparatus of the present invention with a broken away portion revealing the strain gage mechanism and a human subject depicted in phantom.

FIG. 2 is a front elevational view of the apparatus of the present invention.

Figure 3:
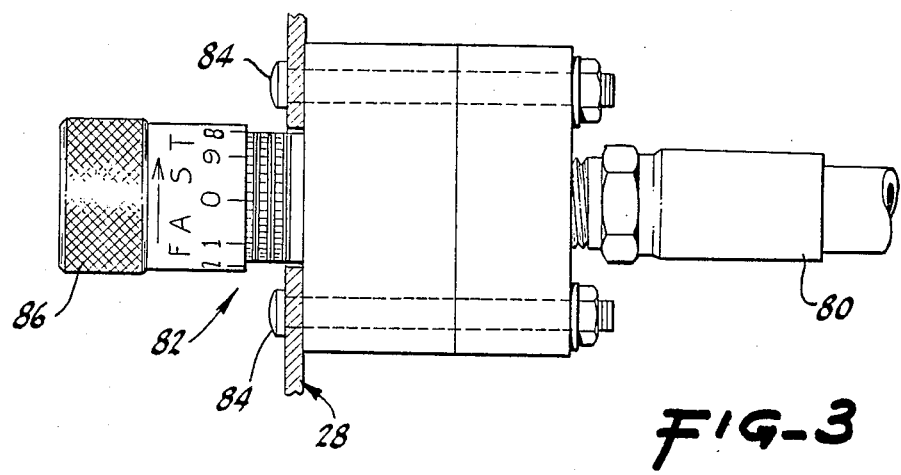
FIG. 3 is an enlarged front elevational view of valve means associated with the hydraulic cylinder.

For a better understanding of the invention reference is made to the following detailed description of the preferred embodiments hereof which should be referenced to the hereinabove described drawings.

DESCRIPTION OF THE PREFERRED EMBODIMENTS

Various aspects of the present invention will evolve from the following detailed description of the preferred embodiments thereof which should taken in conjunction with the prior described drawings.

The invention as a whole is shown in the drawings by reference character 10. The signal generating apparatus 10 includes as one of its elements clamp means 12 for holding the leg 14 of a patient 16. As shown in FIG. 1, subjector patient 16 is seated on a platform 18 in the form of a chair 20. Back rest 22 and gripping handles 24 and 26, as well as, plurality of supports 28 further constitute chair 20. As is apparent from FIG. 1, clamp means 30 is also depicted in FIGS. 1 and 2 for holding the rotating biological limb of subject 16 in the form of leg 14. Clamp jaw 32 opens to accept and hold leg 14 near the ankle region. Adjusting knob assembly 34 permits clamp jaw 32 to move upwardly and downwardly. The position of clamp jaw 32 relative to leg 14 is determined by the position of knob assembly 34 along slot 36. Threaded shaft 38 of knob assembly 34 engages jaw clamp 32, in this regard. Slot 36 in located in member 40 which is supported downwardly from member 42. Member 22 connects to an end piece 44 which is pivotally attached, via pivot member 48, to yoke 46 which is an extension of platform 18. Strap 50 holds the upper portion of leg 14 through cleat 52. Of course, the subject hands, exemplified by hand 53, grasp handles 24 and 26 during operation of apparatus 10

A potentiometer 54, such as an Econo-Pot, Mark 4, 100 k ohm, 1% produces an analog signal through conductor 56 which serves as means 58 for indicating the angular rotation of arm 60 about pivot member 62. Potentiometer 54 mounts to bracket 55 fixed to platform 18. The rotating portion of potentiometer terms with arm 60. Arm 60 is linked to member 42 and clamp means 30 by connector 64, rotatably linked to pivot members 66 and 68. Extension 70 affixes to member 42 and also pivotally attaches to pivot member 68. Thus, potentiometer 54 produces a signal representing the rotation of leg 14.

Means 72 is also included in the present invention for measuring the force exerted by leg 14 in its rotation within clamp means 30. Means 72 may include as one of its elements a hydraulic cylinder 74 having a piston shaft 76 extended therefrom and pivotally connected to pivot member 68. Hydraulic cylinder may take the form of a model 81710-DUZ, manufactured by Bimba Co. of Mone Ill. Hydraulic lines 78 and 80 pass hydraulic fluid to needle valve 82 which is bolted to platform 18 by plurality of bolts 84. Adjustment control 86 permits the user to increase or decrease the resistance to flow of hydraulic fluid through hydraulic lines 78 and 80 and through hydralic cylinder 74. Thus, shaft 76, and a piston attach thereto within hydraulic cylinder 74 (not shown), requires a commensurate amount of force for its movement dependent of the position of valve 82. In other words, valve 82 controls the amount of force to move shaft 76 in and out of hydraulic cylinder 74. Valve 82 may be needle valve Model 12EV manufactured by Parke Co. of Elvira, Ohio.

Attach to hydraulic cylinder 74 is a strain gage 88. Strain gage 88, of course, serves as a transducer for the force applied thereto by hydraulic cylinder 74. Strain gage 88 is connected to frame member 90 which is fixed to chair 20. Conductor 92 carries an analog signal representing the force applied by hydraulic cylinder 74, and through the prior described linkage, the force exerted by leg 14.

Figure 4:
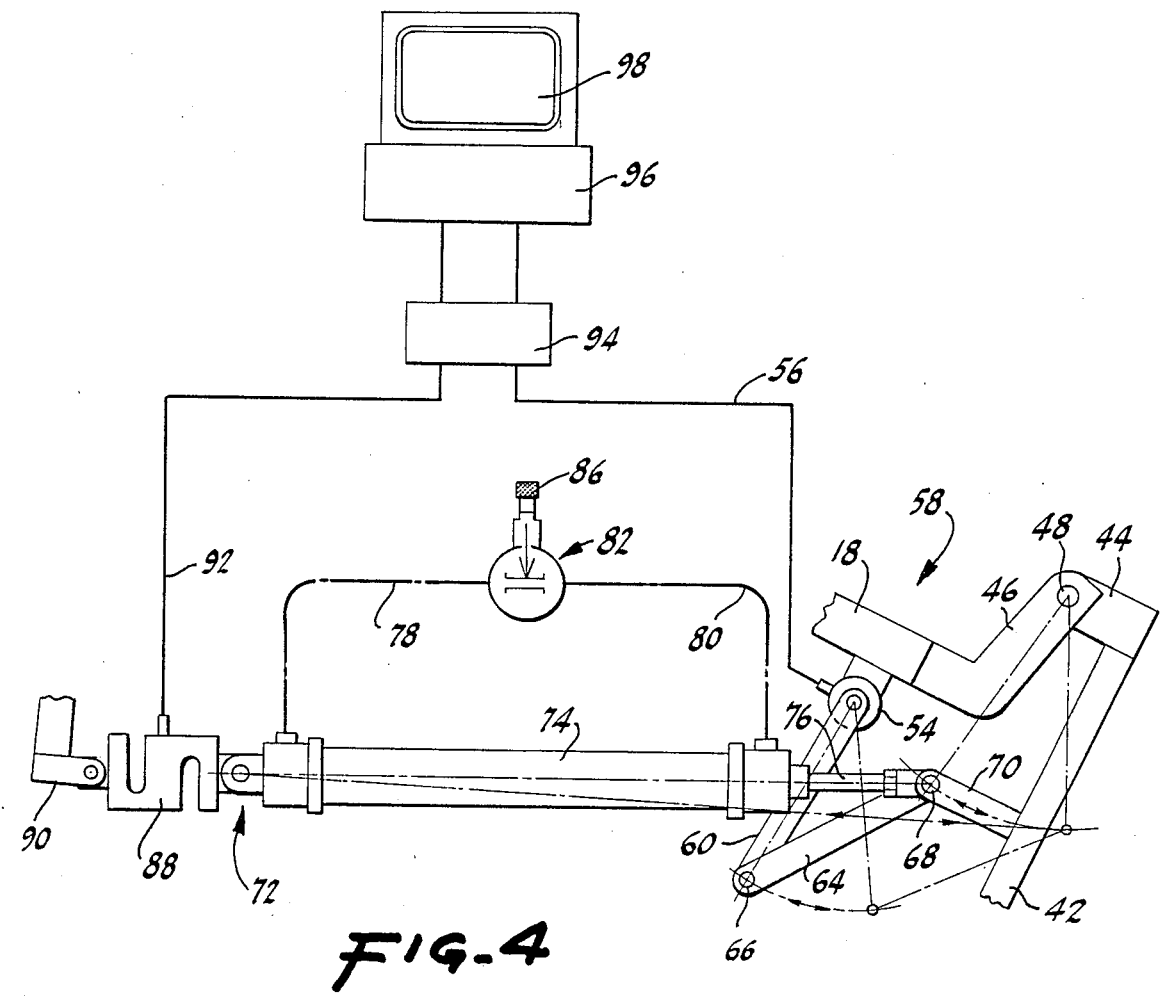
FIG. 4 is a side elevational view of a portion of mechanical linkage of the apparatus of the present invention and depicting the electronic appurtenances in schematic.

With reference to FIG. 4 it may be seen that means 58 for measuring the angular rotation of leg 14 and means 72 for measuring the force exerted by leg 14 are interrelated. Conductors 56 and 92 feed analog signals into analog-to-digital converter 94 which may be employed in a microprocessor 96 having a video display 98. Analog-to-digital converter 94 may take the form of a Model PC40, manufactured by Computer Continuum of Daly City, Ca. Microprocessor 96 may take the form of an Extra, Model 2, manufactured by ITT, Corp. of San Jose, Calif. Analog-to-digital converter 96 may be fixed to frame member 100 of chair 20.

In operation, the user sits on platform 18 of chair 20. Leg 14 is fixed to clamp means 30 by clap jaws 32 approximately 4 inches above the ankle of leg 14. Strap 50 is also employed to hold the thigh of leg 14 to platform 18, in this regard. The user grips handles 24 and 26 and raises leg 14. Preliminary measurements are made with microprocessor 98 to ascertain the rest and extension position of leg 14. Needle valve 82 is adjusted to obtain a desirable angular rate of movement of leg 14 of, e.g.: between 30 and 40 degrees per second. Such rate of movement may be manually clocked or automatically clocked by the microprocessor 94. The user 16 then extends and flexes leg 14 using a maximum effort. Knee torque is measured using the inputs from the potentiometer 62 and strain gage 88. In this way, "peak" torque may be measured for leg 14 and used for the sake of comparison with the "peak" torque of the other leg of subject 16. Also, device 10 may be used to exercise or rehabilitate a weak leg, utilizing the accurate torque measurements therefrom.

While in the foregoing, embodiments of the invention have been set forth in considerable detail for the purposes of making a complete disclosure of the invention it may be apparent to those of skill in the art that numerous changes may be made in such details without departing from the spirit and principles of the invention.

What is claimed is:

1. An apparatus for obtaining a signal representing a measurement of the torque produced by a rotating biological limb, comprising:
   a. clamp means for holding the rotating biological limb;
   b. an arm, including means linking said arm to said clamp means;
   c. a pivot member, said arm rotatably connected to said pivot member;
   d. means for measuring the angular rotation of said arm about said pivot member;
   e. means for measuring the force exerted by the rotating biological limb on said clamp means simultaneously with said measurement of the angular rotation of said arm, said means including a strain gage linked to said clamp means.

2. The apparatus of claim 1 in which additionally-comprises regulating means for providing mechanical resistance to said rotation of said arm.

3. The apparatus of claim 2 in which said regulating means for providing mechanical resistance to said rotation of said arm includes a hydraulic cylinder mechanically linked to said strain gage.

4. The apparatus of claim 3 which further comprises adjusting means for determining the level of mechanical resistance provided by said regulating means.

5. The apparatus of claim 4 in which said adjusting means includes valve means for controlling the flow of hydraulic fluid through said hydraulic cylinder.

6. The apparatus of claim 5 which additionally comprises a platform, said clamp means pivotally connected to said platform and said pivot member being connected to said platform.

7. The apparatus of claim 1 in which said means linking said arm to said clamp means includes an appendage pivotally attached to said arm and pivotally attached to said clamp means.

8. The apparatus of claim 7 which additionally comprises regulating means for providing mechanical resistance to said rotation of said arm.

9. The apparatus of claim 8 which additionally comprises a platform, said clamp means pivotally connected to said platform.

10. The apparatus of claim 9 in which said clamp means is pivotally connected to said platform, and said pivot member is connected to said platform.

11. The apparatus of claim 10 in which said regulating means includes a hydraulic cylinder mechanically linked to said strain gage and valve means for controlling the flow of hydraulic fluid through said hydraulic cylinder.

12. The apparatus of claim 11 in which said valve means is mounted on said platform.

* * * * *